(12) United States Patent
Kimura et al.

(10) Patent No.: US 9,257,156 B2
(45) Date of Patent: Feb. 9, 2016

(54) ELECTROMAGNETIC WAVE SIGNAL PROCESSOR AND ELECTROMAGNETIC WAVE DETECTOR

(71) Applicant: KABUSHIKI KAISHA TOSHIBA, Minato-ku, Tokyo (JP)

(72) Inventors: Shunsuke Kimura, Kawasaki (JP); Hideyuki Funaki, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 28 days.

(21) Appl. No.: 14/299,103

(22) Filed: Jun. 9, 2014

(65) Prior Publication Data
US 2014/0368184 A1    Dec. 18, 2014

(30) Foreign Application Priority Data
Jun. 14, 2013   (JP) ................................. 2013-125987

(51) Int. Cl.
*G01R 13/02*    (2006.01)
*G11C 7/00*    (2006.01)
(Continued)

(52) U.S. Cl.
CPC .............. *G11C 7/00* (2013.01); *G01N 23/2251* (2013.01); *G01R 13/0218* (2013.01); *G01R 19/2506* (2013.01); *G01R 19/2509* (2013.01); *G01R 27/02* (2013.01); *H04N 5/335* (2013.01)

(58) Field of Classification Search
CPC .. G01R 13/00; G01R 13/0218; G01R 13/345; G01R 19/2506; G01R 19/2509; G01R 27/02; G11C 7/00; G01N 23/2251; G01T 1/2914; H04N 5/335
USPC .......... 324/76.11, 76.12, 76.56, 103 P, 103 R, 324/144, 255, 676, 710, 750.12; 702/1, 57, 702/66, 75, 78, 108, 115
See application file for complete search history.

(56) References Cited

U.S. PATENT DOCUMENTS 4,118,625 A * 10/1978 Underwood ........... G01N 21/51
                                                            250/343
4,167,753 A *  9/1979 Lynk .................... G01S 7/52026
                                                            348/163
(Continued)

FOREIGN PATENT DOCUMENTS

GB           1151804        5/1969
JP           6-180369       6/1994
(Continued)

OTHER PUBLICATIONS

Extended European Search Report issued by the European Patent Office on Aug. 4, 2015, for European Patent Application No. 14170260.5.

*Primary Examiner* — Hoai-An D Nguyen
(74) *Attorney, Agent, or Firm* — Finnegan, Henderson, Farabow, Garrett & Dunner, L.L.P.

(57) ABSTRACT

There is provided an electromagnetic wave signal processor configured to process an input pulse signal corresponding to an electromagnetic wave, comprising a signal processing unit including: a peak detecting circuit to detect peak values of each amplitude of the input pulse signal; an AD converter to convert the peak values into digital signals; a memory device comprising memory cells each having an address assigned in accordance with each of values capable of being taken by the digital signals of the peak values, and being able to have any one of a plurality of internal states representing detection frequencies of the peak values; and a writing circuit to change the internal state in the memory cell that has the address corresponding to the value of each digital signal converted by the AD converter, so as to increment the detection frequency represented by the internal state.

8 Claims, 7 Drawing Sheets

(51) Int. Cl.
*G01R 19/25* (2006.01)
*G01R 27/02* (2006.01)
*H04N 5/335* (2011.01)
*G01N 23/225* (2006.01)

(56) References Cited

U.S. PATENT DOCUMENTS 5,225,682 A 7/1993 Britton, Jr. et al.
8,819,859 B1 * 8/2014 Huang ................... G01N 21/35
　　　　　　　　　　　　　　　　　　　　250/306

2009/0082981 A1 * 3/2009 Muto ................. G01R 19/2506
　　　　　　　　　　　　　　　　　　　　702/77
2010/0066596 A1 * 3/2010 Tyree .................... F41G 7/2213
　　　　　　　　　　　　　　　　　　　　342/195

FOREIGN PATENT DOCUMENTS

| JP | 6-331750 | 12/1994 |
| JP | 2002-55171 | 2/2002 |
| JP | 2002-107300 | 4/2002 |
| JP | 2007-132764 | 5/2007 |
| JP | 2009-175042 | 8/2009 |

* cited by examiner

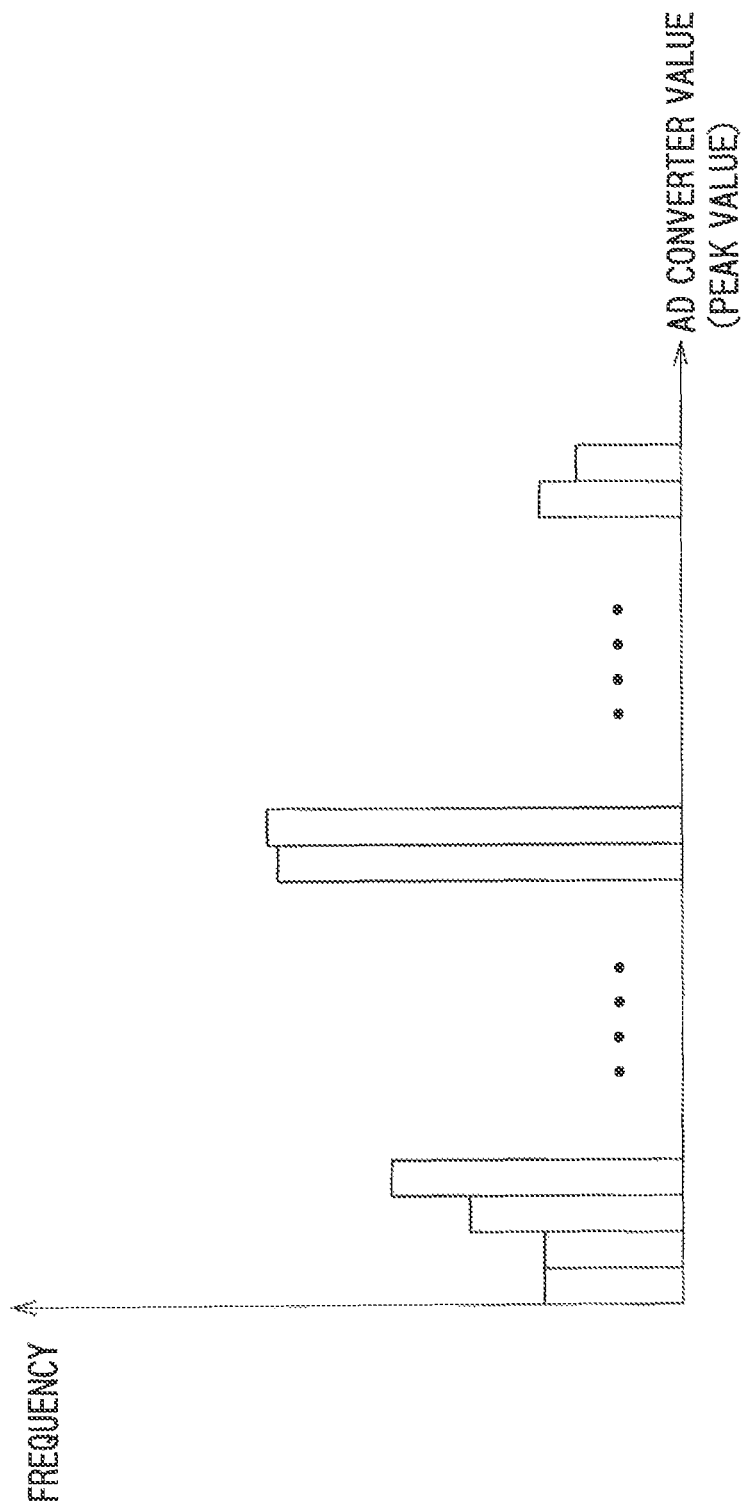
F I G. 5

ELECTROMAGNETIC WAVE SIGNAL PROCESSOR AND ELECTROMAGNETIC WAVE DETECTOR

CROSS-REFERENCE TO RELATED APPLICATIONS

This application is based upon and claims the benefit of priority from Japanese Patent Application No. 2013-125987, filed Jun. 14, 2013; the entire contents of which are incorporated herein by reference.

FIELD

An embodiment described herein relates to an electromagnetic wave signal processor and an electromagnetic wave detector.

BACKGROUND

A multi-channel analyzer has functions that mainly include waveform shaping of an analog input pulse, AD conversion of a waveform-shaped signal, peak detection based on digital signals, and creation of a peak value frequency distribution.

As a related art, there is a multi-channel analyzer which subjects digital values obtained through the AD conversion to signal processing with a digital signal processing circuit to find peak values, and creates the peak value frequency distribution.

With this circuit configuration, there is a problem in that AD values of a pulse other than the peak values are also imported into the digital signal processing circuit to perform calculation for finding peak values, which increase the amount of digital data imported into the digital signal processing circuit and the amount of computation. In particular, this problem is more prominent when the number of input terminals is increased due to multichanneling. In this circuit configuration, since a counting rate is determined by the number of computation and a clock in digital signal processing, the counting rate declines as the number of steps in the digital signal processing is increased.

BRIEF DESCRIPTION OF THE DRAWINGS

FIG. 5 schematically shows an example of a peak value frequency distribution;

DETAILED DESCRIPTION

According to one embodiment, there is provided an electromagnetic wave signal processor configured to process an input pulse signal corresponding to an electromagnetic wave, the electromagnetic wave signal processor comprising at least one signal processing unit, and the signal processing unit includes a peak detecting circuit, an AD converter, a memory device and a writing circuit.

The peak detecting circuit detects peak values of each amplitudes of the input pulse signal.

The AD converter converts the peak values into digital signals.

The memory device includes a plurality of memory cells each of the memory cells having an address assigned in accordance with each of values capable of being taken by the digital signals of the peak values, and each of the memory cells being able to have any one of a plurality of internal states representing detection frequencies of the peak values and be changed among the plurality of internal states.

The writing circuit changes the internal state in the memory cell that has the address corresponding to the value of each of the digital signals converted by the AD converter, so as to increment the detection frequency represented by the internal state.

Below, the embodiment of the present invention will be described with reference to the drawings.

Figure 1:
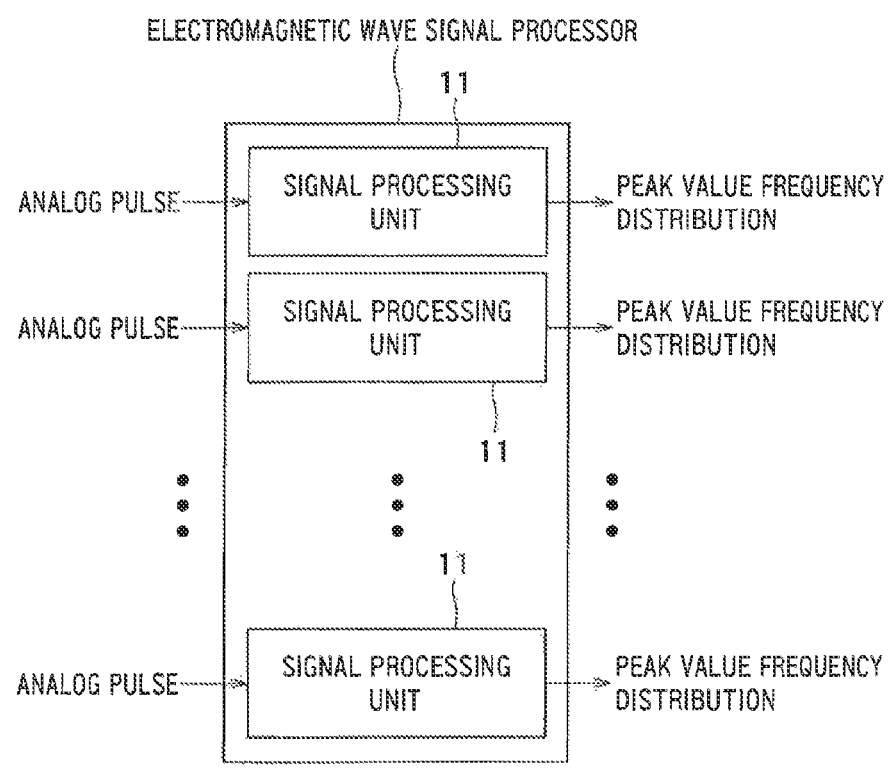
FIG. 1 shows an electromagnetic wave signal processor according to the present embodiment.

FIG. 1 is a block diagram showing an electromagnetic wave signal processor according to the present embodiment.

The electromagnetic wave signal processor of FIG. 1 includes a plurality of signal processing units 11 arranged corresponding to different signal sources. Each signal processing unit 11 creates a peak value frequency distribution of an analog pulse output from the signal source corresponding thereto.

Each signal source is a detector for an electromagnetic wave such as an X-ray and light. Each signal source corresponds to one of different pixels. Pixel values are determined based on the frequency distributions created by the signal processing units 11, and the pixel values are arranged to create an image. When an X-ray detector is used as the signal source, a CT image can be created based on X-ray energies detected by the X-ray detectors.

Each signal processing unit 11 may be configured by one chip, or a chip may include a plurality of signal processing units.

Figure 2:
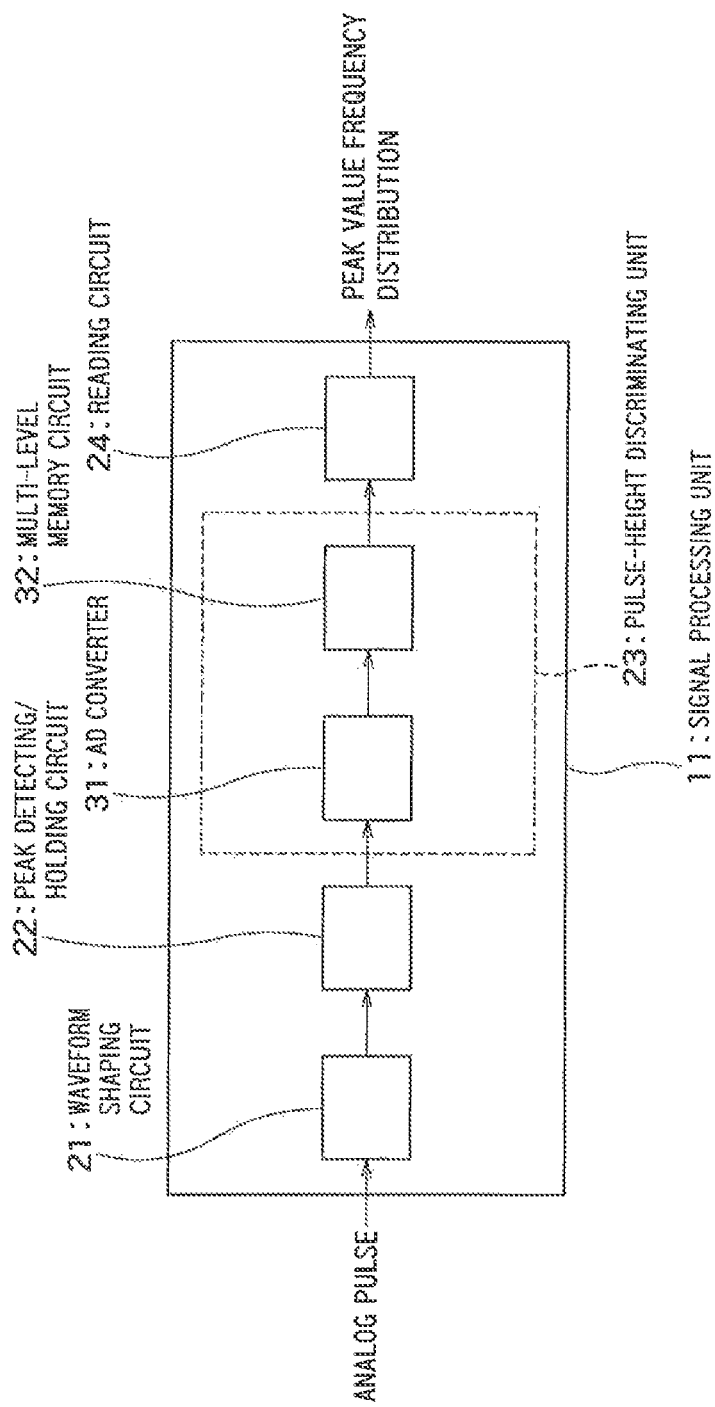
FIG. 2 shows a block configuration of a signal processing unit shown in FIG. 1.
Figure 4:
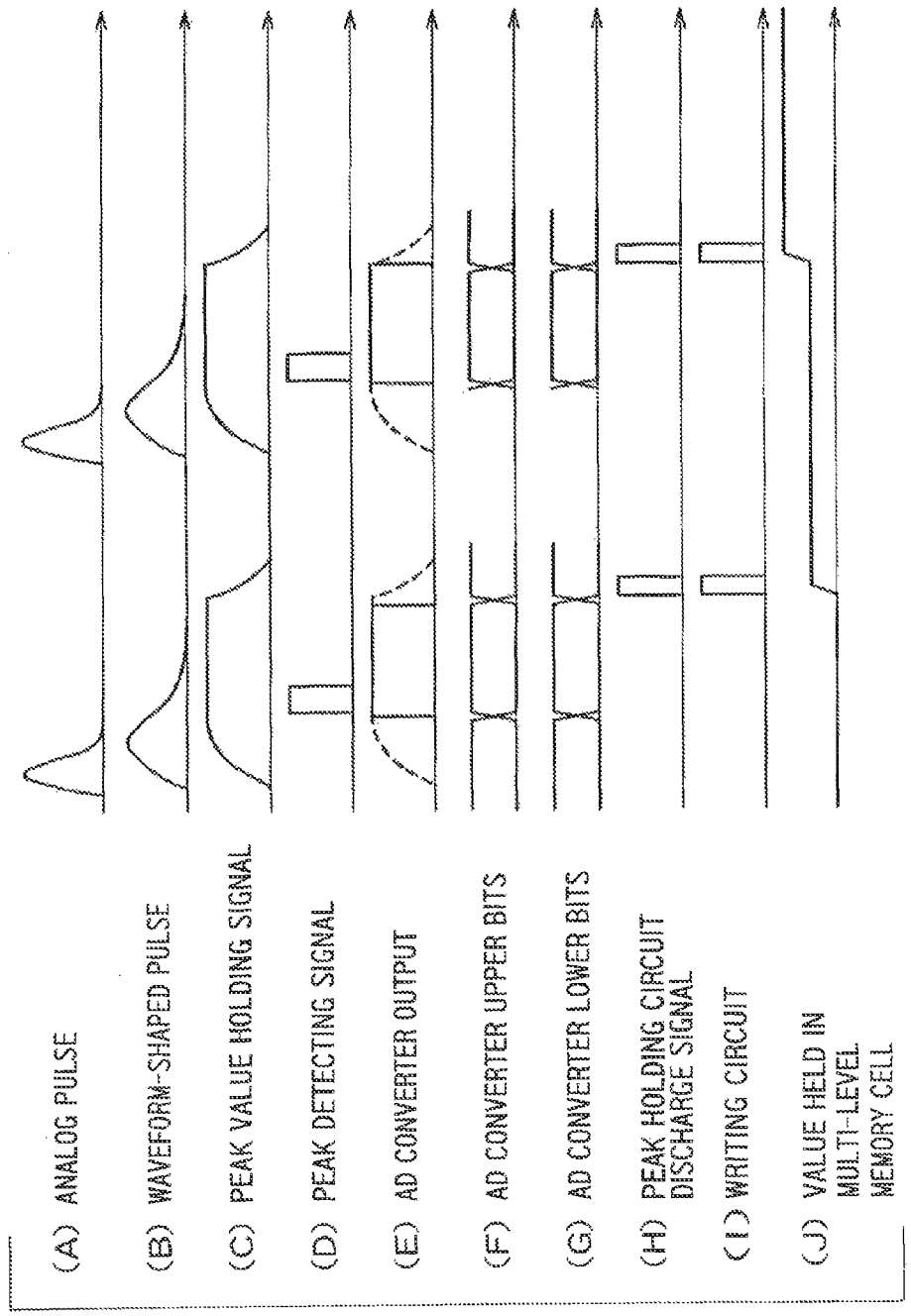
FIG. 4 shows a timing diagram of signal processing performed in the signal processing unit.

FIG. 2 is a block diagram of the signal processing unit shown in FIG. 1. Since the signal processing units included in the electromagnetic wave signal processor of FIG. 1 each have the same configuration, FIG. 2 shows only the configuration of a single signal processing unit. In addition, FIG. 4 shows a timing diagram of signal processing performed in the signal processing unit 11.

The signal processing unit 11 includes a waveform shaping circuit 21, a peak detecting/holding circuit 22, a pulse-height discriminating unit 23, and a reading circuit 24. The pulse-height discriminating unit 23 includes an AD converter 31 and a multi-level memory circuit 32.

The waveform shaping circuit 21 shapes an analog pulse input from a signal source being an object to which pulse-height analysis is performed, into any pulse form. The waveform-shaped pulse is received by the peak detecting/holding circuit 22 in the next stage. FIG. 4(A) shows an example of the analog pulse input from the signal source. In addition, FIG. 4(B) shows an example of a pulse obtained by performing the waveform shaping to the analog pulse. In the example of FIG. 4(B), the waveform shaping is performed so as to elongate the analog pulse.

The peak detecting/holding circuit 22 detects the peak values of amplitudes of a pulse input from the waveform shaping circuit 21, and holds signals of the peak values. The peak detecting/holding circuit 22 further outputs peak detection signals to the AD converter 31 at the points in time when the peak values are detected. The peak detecting/holding circuit 22 may be configured by an analog circuit that uses, for example, a comparator, a current source, a capacitor, a switch, and the like. FIG. 4(C) shows an example of the signals of the peak values held by the peak detecting/holding circuit 22. In addition, FIG. 4(D) shows an example of the peak detection signals.

Note that a filtering circuit such as a pole compensating circuit may be provided between the peak detecting/holding circuit 22 and the waveform shaping circuit 21. In this case, a signal obtained by filtering an output from the waveform shaping circuit 21 is input into the peak detecting/holding circuit 22.

The signals of the peak values held by the peak detecting/holding circuit 22 is subjected to AD conversion by the AD converter 31 in the next stage. The AD converter 31 performs the AD conversion to the signals of the peak values held by the peak detecting/holding circuit 22 upon receiving the peak detection signals from the peak detecting/holding circuit 22, and outputs digital signals of the peak values to the multi-level memory circuit 32. FIG. 4(E) shows an example of the digital signals output from the AD converter.

The multi-level memory circuit 32 includes a memory device that has a plurality of memory cells. The memory cells each have an address assigned in accordance with each of values that the digital signals of the peak values can take.

Furthermore, each memory cell can have any one of a plurality of internal states. The plurality of internal states represent detection frequencies of the peak values, respectively. For example, the plurality of internal states correspond to integers between zero and an upper limit value inclusive, respectively. The internal state in each memory cell makes a transition (i.e., is changed) by writing made from the writing circuit 33 to be described later.

The multi-level memory circuit 32 accesses a memory cell that has an address corresponding to a value of each of the digital signals of the peak values, and changes the internal state in the memory cell so as to increment a value of the detection frequency represented by the internal state by one. By repeating such a process every time the peak value is detected, a peak value frequency distribution representing frequencies of the peak values can be obtained based on the internal states in the memory cells. Hereinafter, the multi-level memory circuit 32 will be described in detail.

Figure 3:
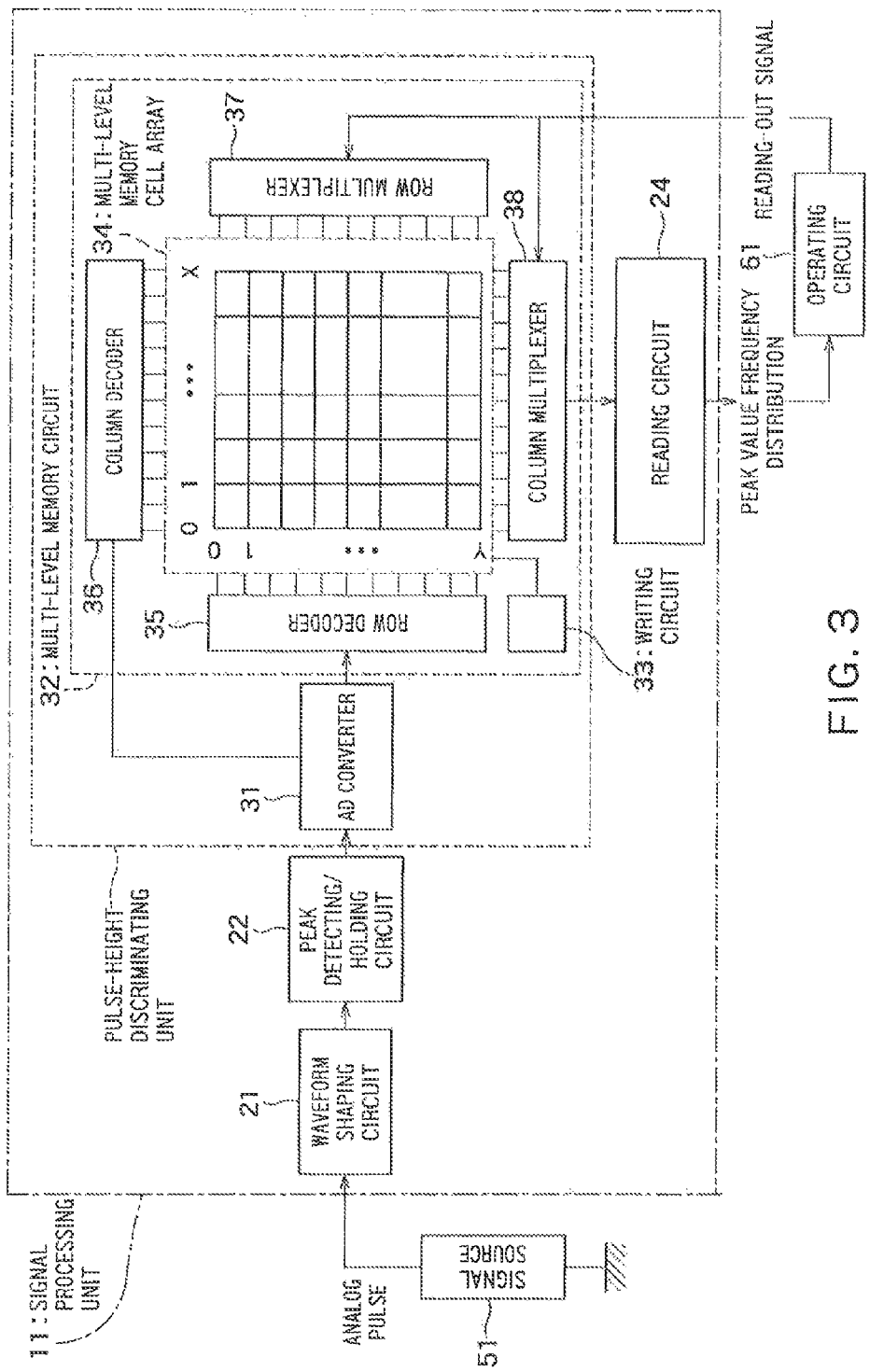
FIG. 3 shows a detailed example configuration of a multi-level memory circuit, and a signal source and an external circuit connected to the signal processing unit.

FIG. 3 shows a specific configuration example of the multi-level memory circuit 32 included in the signal processing unit 11, a signal source 51 connected to the signal processing unit, and an external circuit (operating circuit) 61.

The multi-level memory circuit 32 includes a row decoder 35, a column decoder 36, a multi-level memory cell array (memory device) 34, a writing circuit 33, a row multiplexer 37, and a column multiplexer 38.

The multi-level memory cell array 34 has a plurality of memory cells arranged in a matrix pattern. To each memory cell, an address is assigned which has one of the values that the peak values can take. The address includes a row address and a column address.

The memory cell is an analog memory cell, or a memory cell that can hold a value as digital value. Each memory cell has a plurality of internal states each representing an integer, for example, between zero and an upper limit value inclusive. Such a memory cell may be configured by making use of, for example, a capacitor, or a next-generation non-volatile memory such as a NAND flash memory, an MRAM, and a ReRAM.

In the present embodiment, a capacitor is assumed as the memory cell. In the case where a capacitor is used, the potential (internal state) thereof is changed by writing a certain amount of electric charge to the capacitor every time the memory is accessed. The number of accesses (frequency) can be identified based on the potential. With an MRAM, the number of accesses can be stored by changing the magnetic resistance (internal state) thereof.

The row decoder 35 receives a predetermined number of bits (upper bits) on the upper side of an AD-converted value output from the AD converter 31, and identifies a row address of the memory cell to be accessed based on the upper bits. The column decoder 36 receives remaining lower bits of the AD-converted value output from the AD converter, and identifies a column address of the memory address to be accessed based on the lower bits.

As an alternative configuration, a configuration may be used in which the column decoder 36 identifies the column address based on the upper bits, and row decoder 35 identifies the row address based on the lower bits.

The memory cell that has the row address and the column address identified by the row decoder 35 and the column decoder 36 is accessed.

The process to divide the AD-converted value into the upper bits and the lower bits may be performed by the AD converter 31, or in a multi-level memory cell circuit 34. The configuration example shown in FIG. 3 illustrates the case where the process is performed by the AD converter 31. FIG. 4(F) and FIG. 4(G) show examples of signals of the upper bits and the lower bits in the AD-converted value, respectively.

The writing circuit 33 writes a certain amount of electric charge to a memory cell identified by the row decoder 35 and the column decoder 36. FIG. 4(I) shows an example of output signals of the writing circuit 33. A held value (voltage) of the memory cell is increased by a certain value every time the electric charge is written. FIG. 4(J) shows an example of the voltages held by the memory cell. By writing made from the writing circuit 33, the internal state in the memory cell is changed, for example, so as to be incremented by one. By repeating this, the peak value frequency distribution (pulse-height frequency distribution) can be obtained in the form of a set of the internal states in the memory cells.

As a variation, a configuration may be conceived in which the internal state in the memory cell is changed every time the memory cell is accessed a plurality of times (N times). In this configuration, each internal state represents a value of a certain range. A circuit to store the number of accesses (up to N times) needs to be provided to each memory cell. According to this method, although a calculated frequency may have a certain error, a high frequency can be stored even in the case where the number of the internal states that the memory cell can take is small.

The row multiplexer 37 and the column multiplexer 38 specify the row address and the column address in accordance with a read-out signal given from an external operating circuit 61. The reading circuit 24 reads out a value of the internal state in the memory cell from the memory cell corresponding to the specified row address and column address. The reading circuit 24 outputs the value of the internal state read out of the memory cell, to the external operating circuit 61.

The operating circuit 61 is configured by, for example, an FPGA, a processor, or the like. The operating circuit 61 outputs a read-out signal after a given measurement time from the start of measurement in order to sequentially read out the internal states in a memory cell group through the reading circuit 24. The external operating circuit 61 is provided with information about an association between a memory address and a peak value, and an association between an internal state and a frequency (the number of accesses), in advance. The external operating circuit 61 converts the values of the internal states in memory cells into a peak value frequency distribution, based on these pieces of information. FIG. 5 shows an image of the peak value frequency distribution. Such a frequency distribution is obtained for each signal processing unit of FIG. 1.

The external operating circuit 61 determines a pixel value (e.g., a density value) of the pixel corresponding to the each signal processing unit based on the peak value frequency distribution. Then, the pixel values are arranged to obtain an image (e.g., a CT image).

Figure 6:
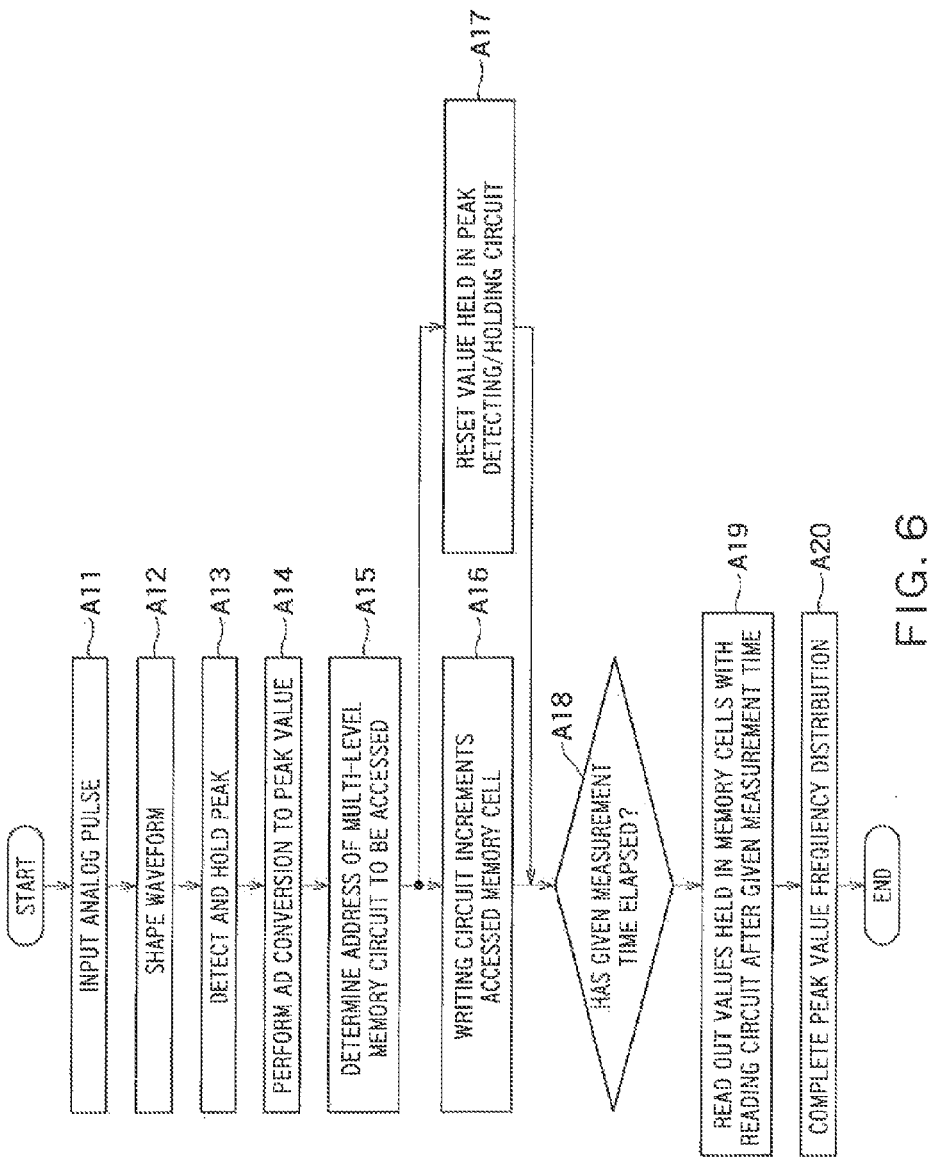
FIG. 6 shows a signal processing flow according to the present embodiment.

FIG. 6 shows a signal processing flow according to the present embodiment.

Measurement is started at any point in time. An analog pulse is input into the waveform shaping circuit 21 from the signal source 51 (A11).

The waveform shaping circuit 21 performs the waveform shaping to the input analog pulse and outputs it to the peak detecting/holding circuit 22 in the next stage (A12).

The peak detecting/holding circuit 22 detects the peaks of the signal shaped by the waveform shaping circuit 21, and holds the values of the detected peak signals (A13).

The AD converter performs the AD conversion on the values of the peak signals held by the peak detecting/holding circuit 22 (A14).

The multi-level memory circuit 32 identifies a memory address (a row address and a column address) to be accessed based on the upper bits and the lower bits in a bit string of the AD-converted value, with the row decoder 35 and the column decoder 36 (A15). The identification of the address by the multi-level memory circuit 32 triggers the writing circuit 33 to output a discharge signal.

The peak detecting/holding circuit 22 resets (discharges) the held value based on the discharge signal output from the writing circuit 33 (A17). This causes the peak detecting/holding circuit 22 to prepare for the next input of an analog pulse.

Furthermore, the writing circuit 33 accesses the memory cell corresponding to the memory address identified in step A15, and changes the internal state in the memory cell so as to increment it by one (A16).

The writing circuit 33 or a controlling circuit (not shown) determines whether or not a given measurement time has elapsed from the start of measurement, with a timer (A18). The processes from the inputting of the analog pulse to the writing to the memory cell (A11 to A17) are repeated until the given measurement time elapses.

When the given measurement time has elapsed, the reading circuit 24 reads out the internal states in the memory cells and outputs them to the external operating circuit 61 (A19). The external operating circuit 61 obtains a peak value frequency distribution from a set of the internal state values of the memory cells read out by the reading circuit 24 (A20).

As described above, according to the present embodiment, values of the peak signals detected by the peak detecting/holding circuit 22 are subjected to AD conversion, and the internal state in a memory cell that has an address corresponding to the value of each of the digital signals of the peak values is changed so as to be incremented by one. By repeating this, the peak value frequency distribution can be obtained as a set of the internal states in the memory cells. As a result, a digital circuit (digital operation processing) is dispensed with, which can therefore make a circuit area small and can make a counting rate high. Furthermore, data that should be held for a digital operation is also dispensed with, which can make a storage capacity small. Thus, in the present embodiment, the decline of a counting rate and the increase of a circuit scale can be averted.

Figure 7:
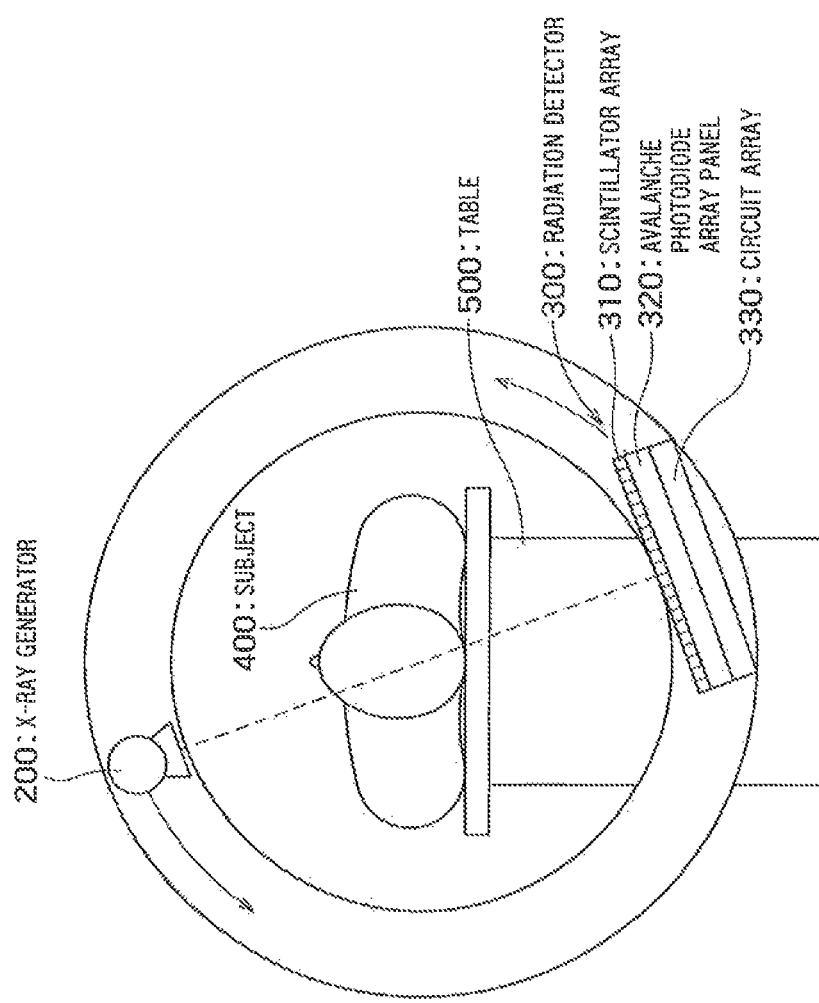
FIG. 7 shows a computed tomographic imaging system according to the present embodiment of the present invention.

FIG. 7 shows a computed tomographic (CT) imaging system as an electromagnetic wave imaging device according to the embodiment of the present invention. This CT system includes an X-ray generator (electromagnetic wave generator) 200, and a radiation detector (electromagnetic wave detector) 300.

The radiation detector 300 includes a scintillator array 310, an avalanche photodiode (APD) array panel 320, and a circuit array 330.

The circuit array 330 includes the electromagnetic wave signal processors and the operating circuits according to the present embodiment. The operating circuit may be separated from the circuit array 330 and separately provided as an individual device. The circuit array 330 includes signal processing units each corresponding to an APD of the APD array panel 320. A pair of the scintillator and the APD corresponds to the signal source 51 shown in FIG. 3.

A subject 400 lying on a table 500 is irradiated with an X-ray from the X-ray generator 200, and the X-ray that passes through the subject 400 to be attenuated enters the scintillator array 310 of the radiation detector 300. A photon is generated in the scintillator in proportion to the energy of the entering X-ray. The generated photon is measured by an APD of the APD array panel 320. An analog pulse of a current measured by the APD is input into a signal processing unit corresponding to the APD. The signal processing unit performs the abovementioned processes and outputs information on a set of the internal states in the memory cells to the operating circuit. The operating circuit creates a peak value frequency distribution of each pixel based on the set of internal states in the memory cells output from each signal processing unit. Pixel values are determined based on the peak value frequency distributions, and a CT image (X-ray image) is obtained by arranging the pixel values.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An electromagnetic wave signal processor configured to process an input pulse signal corresponding to an electromagnetic wave, the electromagnetic wave signal processor comprising at least one signal processing unit,
    the signal processing unit comprising:
        a peak detecting circuit to detect peak values of each amplitudes of the input pulse signal;
        an AD converter to convert the peak values into digital signals;
        a memory device comprising a plurality of memory cells each of the memory cells having an address assigned in accordance with each of values capable of being taken by the digital signals of the peak values, and each of the memory cells being able to have any one of a plurality of internal states representing detection frequencies of the peak values and be changed among the plurality of internal states; and a writing circuit to change the internal state in the memory cell that has the address corresponding to the value of each of the digital signals converted by the AD converter, so as to increment the detection frequency represented by the internal state.

2. The electromagnetic wave signal processor according to claim 1, comprising a plurality of the signal processing units.

3. The electromagnetic wave signal processor according to claim 1, wherein the signal processing unit includes a reading circuit to read out information on the internal state in the memory cell.

4. The electromagnetic wave signal processor according to claim 1, wherein the writing circuit changes the internal state in the memory cell by writing a certain amount of electric charge into the memory cell.

5. The electromagnetic wave signal processor according to claim 1, wherein
the memory cell is identified based on a row address and a column address,
the signal processing unit includes a decoding unit to determine one of the row address and the column address based on upper bits of the digital signal, and the other of the row address and the column address based on lower bits thereof, and
the writing circuit changes the internal state in the memory cell that has the row address and the column address identified by the decoding unit.

6. The electromagnetic wave signal processor according to claim 1, wherein the peak detecting circuit receives, as the input pulse signal, an output signal of a signal source which detects an electromagnetic wave to output a current pulse signal.

7. The electromagnetic wave signal processor according to claim 6, wherein the signal processing unit further includes a waveform shaping circuit that performs waveform shaping on the output signal of the signal source, and
the peak detecting circuit receives, as the input pulse signal, an output signal of the waveform shaping circuit.

8. An electromagnetic wave detector comprising:
a plurality of signal sources each of which detects an electromagnetic wave to output a current pulse signal; and
an electromagnetic wave signal processor comprising a plurality of signal processing unit each processing the pulse signal output from each of the signal sources,
each signal processing unit comprising:
a peak detecting circuit to detect peak values of each amplitude of the pulse signal output from each of the signal sources;
an AD converter to convert the peak values into digital signals;
a memory device comprising a plurality of memory cells each of the memory cells having an address assigned in accordance with each of values capable of being taken by the digital signals of the peak values, and each of the memory cells being able to have any one of a plurality of internal states representing detection frequencies of the peak values and be changed among the plurality of internal states; and
a writing circuit to change the internal state in the memory cell that has the address corresponding to the value of each of the digital signals converted by the AD converter, so as to increment the detection frequency represented by the internal state.

* * * * *